(12) United States Patent
Owens

(10) Patent No.: US 6,651,666 B1
(45) Date of Patent: Nov. 25, 2003

(54) VARIABLE CUFF PRESSURE ADAPTER

(76) Inventor: Norman L. Owens, 3644 New Kathleen Rd., Hephzibah, GA (US) 30815

(*) Notice: Subject to any disclaimer, the term of this patent is extended or adjusted under 35 U.S.C. 154(b) by 0 days.

(21) Appl. No.: 10/201,031

(22) Filed: Jul. 23, 2002

(51) Int. Cl.[7] .............................. A62B 9/02; A62B 9/00; A61M 16/00
(52) U.S. Cl. ........................ 128/207.16; 128/207.14; 128/207.15; 128/204.18; 604/96.01; 604/97.01; 604/99.01
(58) Field of Search .................. 128/207.15, 205.24, 128/204.18, 200.22, 200.26, 200.24, 204.15, 204.14, 207.16, 207.14; 604/96.01, 97.01, 98.02, 99.01, 101.01

(56) References Cited

U.S. PATENT DOCUMENTS

| | | | |
|---|---|---|---|
| 2,881,757 A | | 4/1959 | Haverland |
| 2,898,941 A | | 8/1959 | Kilcup |
| 4,020,849 A | * | 5/1977 | Jackson .................. 128/207.15 |
| 4,471,775 A | * | 9/1984 | Clair et al. ............. 128/205.24 |
| 4,751,924 A | * | 6/1988 | Hammerschmidt et al. ...... 128/207.15 |
| 4,825,862 A | * | 5/1989 | Sato et al. .............. 128/207.15 |
| 5,347,998 A | | 9/1994 | Hodson et al. |
| 5,431,154 A | | 7/1995 | Seigel et al. |
| D409,729 S | | 5/1999 | Dreyfus et al. |

FOREIGN PATENT DOCUMENTS

| | | | | |
|---|---|---|---|---|
| GB | 2248783 A | * | 4/1992 | .......... A61M/16/04 |
| WO | WO 02/03176 | * | 3/1992 | .......... A61M/16/04 |

* cited by examiner

Primary Examiner—Glenn K. Dawson
(74) Attorney, Agent, or Firm—Donald R. Schoonover

(57) ABSTRACT

Pressure in a cuff on an endotracheal tube is controlled by a fluid circuit that includes a port on the endotracheal tube, a moisture absorbent barrier covering that port, a one-way valve, a pressure manometer as well as a pilot balloon fluidically connected to the cuff. A thumb wheel is included in one form of the invention to control operation of the one-way valve.

3 Claims, 3 Drawing Sheets

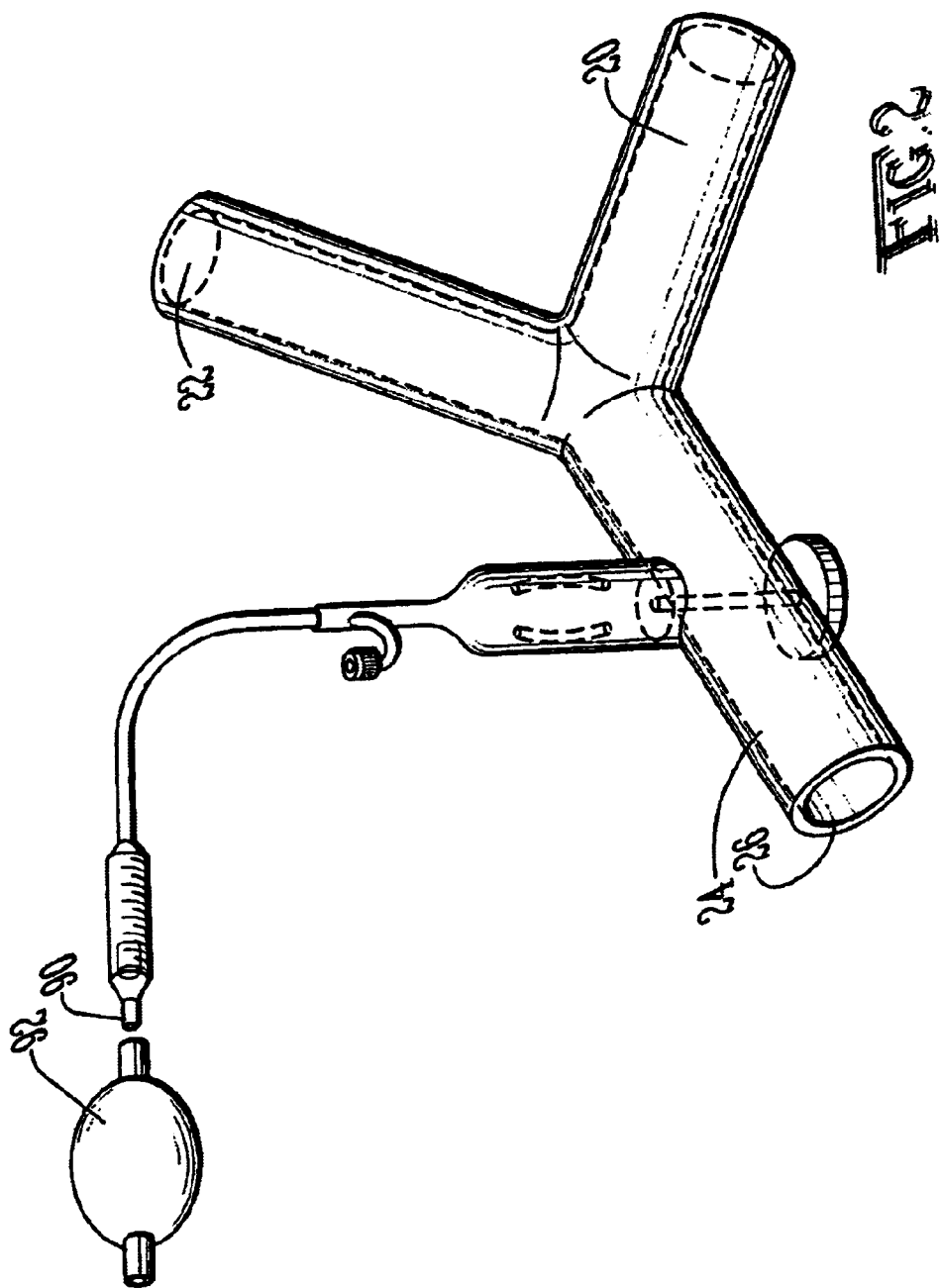

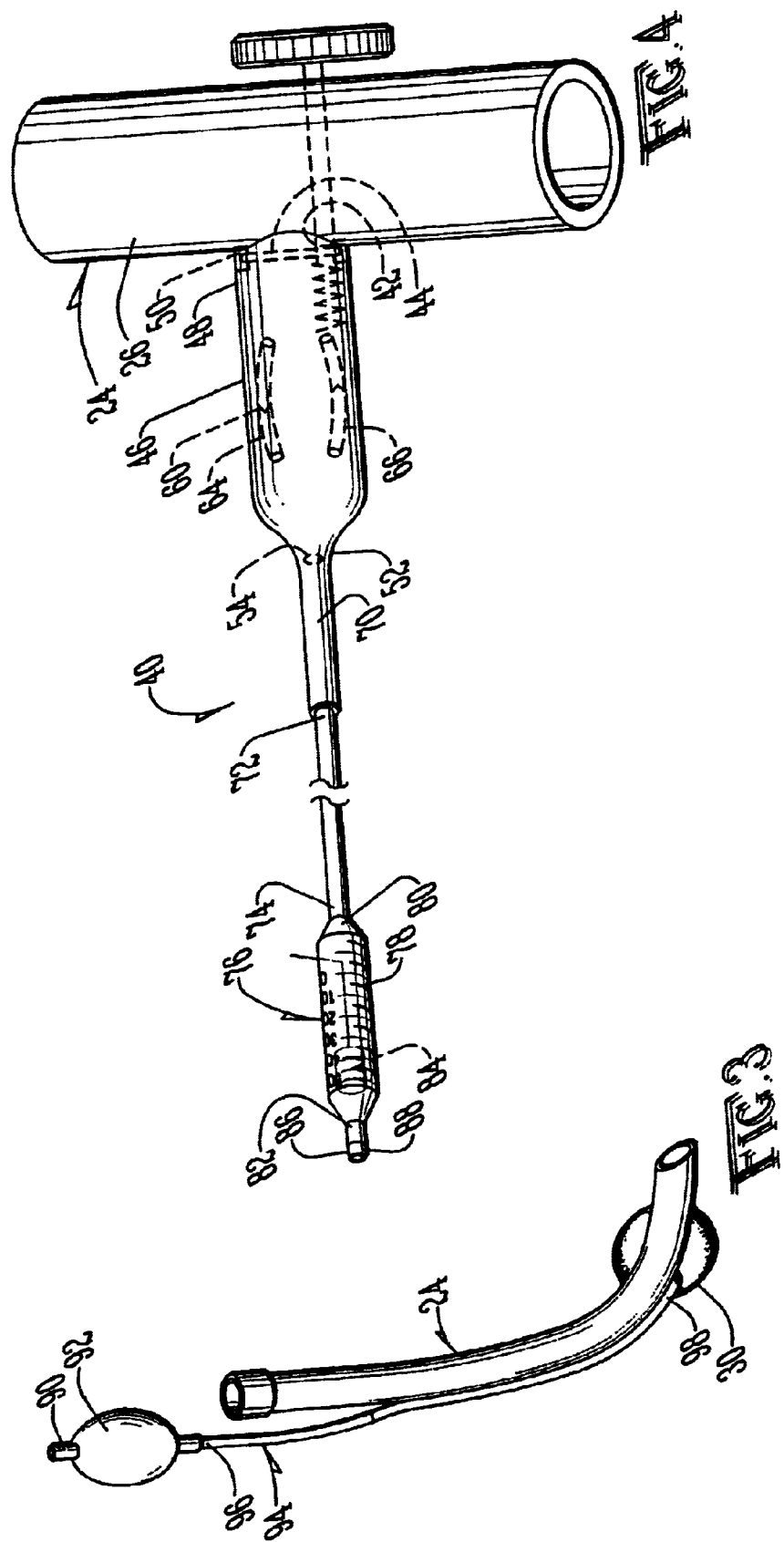

VARIABLE CUFF PRESSURE ADAPTER

BACKGROUND OF THE INVENTION

1. Field of the Invention

The present invention relates to the general art of surgery, and to the particular field of endotracheal tubes.

2. Discussion of the Related Art

Many patients require long-term use of an endotracheal tube. While such devices are very helpful, they have several problems. Some tubes are difficult to keep in place, for example. Some endotracheal tubes include a cuff that is interposed between the endotracheal tube and the patient's tissue. This cuff is intended to seal a volume of air in a patient's lungs.

It has been discovered that, while successful and very helpful in many instances, positive pressure ventilation has risks and complications. Constant high pressure in the cuff and long term positive pressure ventilation is directly related to tracheal stenosis. High pressure decreases blood flow and tissue begins dying adjacent to the cuff during such application of high pressure. During an expiratory phase of a breathing cycle, blood flow is restored.

Therefore, there is a need for an endotracheal tube with a cuff that can remain in place for long periods of time without significant chance of tracheal stenosis.

In some cases, slow leaks can occur because a cuff is either not secure enough or tissue adjacent to the cuff has changed over time. A leak path around the cuff of an endotracheal tube is not desirable. This leak is secondary, the primary leak occurring at the pilot balloon.

Therefore, there is a need for an endotracheal tube system which can remain securely in place to reduce the possibility of slow leaks, yet will not create a significant possibility of tracheal stenosis.

Some endotracheal tube systems include extubation and re-intubation procedures in order to overcome the above-discussed problems. However, in some patients, such as patients with upper airway burns, spasmatic airways or patients who may have an antiphalatic reaction, or the like, these procedures are not an option.

Therefore, there is a need for an endotracheal tube system that can remain securely in place for all patients without requiring extubation and re-intubation.

PRINCIPAL OBJECTS OF THE INVENTION

It is a main object of the present invention to provide an endotracheal tube with a cuff that can remain in place for long periods of time without significant chance of tracheal stenosis while promoting/increasing capillary blood flow during the expiratory phase.

It is another object of the present invention to provide an endotracheal tube system which can remain securely in place to reduce the possibility of slow leaks, yet will not create a significant possibility of tracheal stenosis.

It is another object of the present invention to provide an endotracheal tube system that can remain securely in place for all patients without requiring extubation and re-intubation.

SUMMARY OF THE INVENTION

These, and other, objects are achieved by a variable endotracheal tube cuff pressure controller comprising a positive pressure breathing unit, an endotracheal tube fluidically connected to the positive pressure breathing unit, a cuff on the endotracheal tube, the cuff being located between the endotracheal tube and a patient trachea and a pressure control system which includes a port in the endotracheal tube, a moisture-impervious cover mounted on the endotracheal tube adjacent to the port in the endotracheal tube to cover the port in the endotracheal tube, a one-way valve fluidically connected to the port in the endotracheal tube to permit flow of fluid out of the endotracheal tube via the port in the endotracheal tube and to prevent flow of fluid into the endotracheal tube via the port in the endotracheal tube, a pressure manometer fluidically connected to the one-way valve, and a pilot balloon fluidically connected to the manometer and to the endotracheal tube.

The pressure controller of the present invention permits the cuff to expand sufficiently to prevent direct flow in the manner desired, but will also divert flow from the endotracheal tube during an expiratory phase of a breathing cycle so the cells in the patient's trachea can recover. This provides a fluid-tight fit without creating danger of stenosis in the patient's trachea adjacent to the cuff.

The system embodying the present invention is connected between the patient circuit and the endotracheal/tracheostomy tube. A port is connected to a pilot balloon. During the inspiratory phase of a patient's breathing cycle, pressure/volume is transferred from the patient circuit to the cuff through the pilot balloon. During the expiratory or relax phase, the cuff will deflate to a pressure not less than 15 cm of water which prevents aspiration.

One form of the system embodying the present invention includes a spring that is connected to a thumb wheel to make the controlled pressure adjustable. This allows for lower or higher pressure during the expiratory phase and will optimize pressure to promote an increase in capillary blood flow. During the inspiratory phase, pressure in the cuff is determined by the patient circuit generated by the breathing machine.

BRIEF DESCRIPTION OF THE DRAWING FIGURES

FIG. 2 shows the pressure controller in greater detail.

Figure 1:
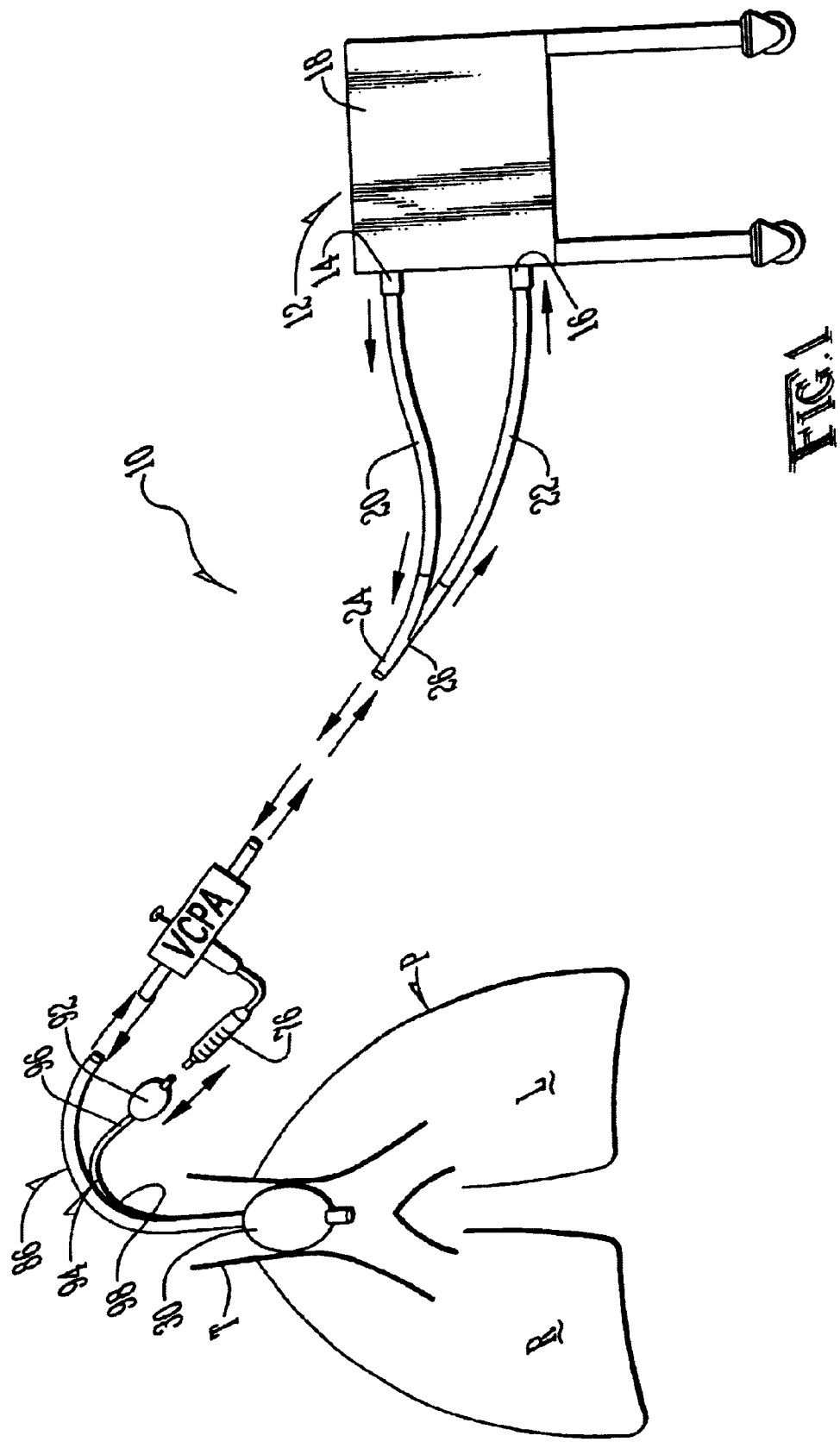
FIG. 1 is a sketch showing the variable endotracheal tube cuff pressure controller embodying the present invention.

FIG. 3 schematically shows the pilot balloon in conjunction with a portion of the endotracheal tube and the cuff on the tube.

FIG. 4 schematically shows the pressure controller embodying the present invention in greater detail.

DETAILED DESCRIPTION OF THE INVENTION

Other objects, features and advantages of the invention will become apparent from a consideration of the following detailed description and the accompanying drawings.

Referring to the figures, it can be understood that the present invention is embodied in a variable endotracheal tube cuff pressure controller 10 which comprises a positive pressure breathing unit 12 which includes an inspiratory port 14, an expiratory port 16 and a unit 18 for moving breathing gas through the inspiratory port 14 and through the expiratory port 16 and fluid conduits associated therewith.

The controller 10 further includes an inspiratory tube 20 an expiratory tube 22 and an endotracheal tube 24 fluidically connected to the inspiratory tube 20 and to the expiratory tube 22. Endotracheal tube 24 includes a wall 26.

A cuff 30 is positioned on the endotracheal tube 24. The cuff 30 is located on the endotracheal tube 24 to be interposed between a trachea T of a patient P and the endotracheal tube 24 to control fluid flow through the trachea and to prevent fluid flow around the endotracheal tube 24. Cuff 30 is inflatable and deflatable as necessary to securely attach the endotracheal tube 24 to the patient.

Controller 10 further includes a pressure control system 40, best shown in FIG. 4, and which includes a port 42 in the wall 26 of the endotracheal tube 24. Port 42 is located to be spaced from cuff 30. A moisture absorbing cover 44 is attached to the wall 26 of the endotracheal tube 24 adjacent to port 42 and is formed of material that is suitable for use in a breathing system of this sort. The cover 44 permits fluid flow through port 42 but blocks moisture. Pressure control system 40 further includes a housing 46 mounted on wall 26 of the endotracheal tube 24 adjacent to port 42. Housing 46 includes a first end 48 fixed to wall 26 adjacent to port 42 in the wall 26 of the endotracheal tube 24. First end 48 includes an inlet port 50 that is fluidically connected to port 42 in the wall 26 of the endotracheal tube 24 with the moisture absorbing cover 44 being interposed between the port 42 in the wall 26 of the endotracheal tube 24 and the inlet port 50 in the housing 46. Housing 46 further includes a second end 52 spaced from first end 48 and includes a rear port 54. Rear port 54 is fluidically connected to the inlet port 50 in the first end 48. A one-way valve 60 is located in the housing 46 and is fluidically interposed between the inlet port 50 and the rear port 54. One-way valve 60 includes flow elements 64 and 66 that permit flow from the inlet port 50 to the rear port 54 and which prevent flow from the rear port 54 to the inlet port 50.

The pressure control system 40 further includes a first fluid conduit 70 having a first end 72 fluidically connected to rear port 54 of the housing 46 and has a second end 74 spaced from the first end 72. A pressure manometer 76 includes a translucent or transparent housing 78 and a first end 80 fluidically connected to second end 74 of first fluid conduit 70 and a second end 82 on the housing 78 of the pressure manometer 76. Second end 82 of the housing 78 of the pressure manometer 76 is in fluid communication with first end 80 of the housing 78 of the pressure manometer 76. A spring-controlled readout 84 is included in the pressure manometer 76.

A second fluid conduit 86 has a first end 88 fluidically connected to second end 82 of the housing 78 of the pressure manometer 76 and a second end 90 spaced from the first end 88 of second fluid conduit 86. A pilot balloon 92 is fluidically connected to second end 90 of second fluid conduit 86 and a third fluid conduit 94 has a first end 96 fluidically connected to the pilot balloon 92 and a second end 98 fluidically connected to cuff 30 on the endotracheal tube 24.

Operation of controller 10 includes fluid flowing out of the endotracheal tube 24 through port 42 past the one-way valve 60 and through the manometer 76 to the pilot balloon 92. Reverse flow from the cuff 30 of the endotracheal tube 24 is not permitted via the one-way valve 60 so the cuff 30 remains securely engaged with the patient's trachea during both the inspiratory and the expiratory phases of the breathing cycle; however, slow leaks do not occur and blood is permitted to flow back to the patient's tissue during the expiratory phase.

One form of the system embodying the present invention includes a spring that is connected to a thumb wheel to make the controlled pressure adjustable. This allows for lower or higher pressure during the expiratory phase and will optimize pressure to promote an increase in capillary blood flow. During the inspiratory phase, pressure in the cuff is determined by the patient circuit 20 generated by the breathing machine 18.

It is understood that while certain forms of the present invention have been illustrated and described herein, it is not to be limited to the specific forms or arrangements of parts described and shown.

I claim:

1. A variable endotracheal tube cuff pressure controller comprising:
   a) a positive pressure breathing unit which includes
      (1) an inspiratory port,
      (2) an expiratory port, and
      (3) a unit for moving breathing gas through the inspiratory port and through the expiratory port;
   b) an inspiratory tube
   c) an expiratory tube
   d) an endotracheal tube fluidically connected to said inspiratory tube and to said expiratory tube, said endotracheal tube including a wall;
   e) a cuff on said endotracheal tube, said cuff being located on said endotracheal tube to be interposed between a trachea of a patient and said endotracheal tube to control fluid flow through a pilot and cuff and to prevent fluid flow around said endotracheal tube; and
   f) a pressure control system which includes
      (1) a port in the wall of said endotracheal tube, the port in the wall of said endotracheal tube being located to be spaced from said cuff,
      (2) a moisture absorbing cover attached to the wall of said endotracheal tube adjacent to the port in the wall of said endotracheal tube,
      (3) a housing mounted on the wall of said endotracheal tube adjacent to the port in the wall of said endotracheal tube, the housing including
         (a) a first end fixed to the wall of said endotracheal tube adjacent to the port in the wall of said endotracheal tube, the first end including an inlet port that is fluidically connected to the port in the wall of said endotracheal tube, the moisture absorbing cover being interposed between the port in the wall of said endotracheal tube and the inlet port in the housing, and
         (b) a second end spaced from the first end of the housing of said pressure control system and which includes a rear port, the rear port being fluidically connected to the inlet port in the first end,
      (4) a one-way valve located in the housing and fluidically interposed between the inlet port and the rear port, the one-way valve including flow elements that permit flow from the inlet port to the rear port and which prevent flow from the rear port to the inlet port,
      (5) a first fluid conduit having a first end fluidically connected to the rear port of the housing and having a second end spaced from the first end,
      (6) a pressure manometer having
         (a) a translucent or transparent housing,
         (b) a first end fluidically connected to the second end of the first fluid conduit, and
         (c) a second end on the housing of the pressure manometer, the second end of the housing of the pressure manometer being in fluid communication with the first end of the housing of the pressure manometer, (7) a second fluid conduit having a first end fluidically connected to the second end of the housing of the pressure manometer and a second end spaced from the first end of the second fluid conduit, (8) a pilot balloon fluidically connected to the second end of the second fluid conduit, and (9) a third fluid conduit having a first end fluidically connected to the pilot balloon and a second end fluidically connected to said cuff on said endotracheal tube.

2. The pressure controller as described in claim 1 wherein said pressure control system further includes a spring connected to the one-way valve and a hand control connected to the spring and mounted on the wall of said endotracheal tube at a location spaced from the port in the wall of said endotracheal tube.

3. A variable endotracheal tube cuff pressure controller comprising:

a) a positive pressure breathing unit;

b) an endotracheal tube fluidically connected to said positive pressure breathing unit;

c) a cuff on said endotracheal tube, said cuff being located between said endotracheal tube and a patient trachea; and d) a pressure control system including (1) a port in said endotracheal tube, (2) a moisture-impervious cover mounted on said endotracheal tube adjacent to the port in said endotracheal tube to cover the port in said endotracheal tube, (3) a one-way valve fluidically connected to the port in said endotracheal tube to permit flow of fluid out of said endotracheal tube via the port in said endotracheal tube and to prevent flow of fluid into said endotracheal tube via the port in said endotracheal tube, (4) a pressure manometer fluidically connected to the one-way valve, and (5) a pilot balloon fluidically connected to the manometer and to said cuff on said endotracheal tube.

\* \* \* \* \*